(12) United States Patent
Broy et al.

(10) Patent No.: US 6,773,577 B1
(45) Date of Patent: Aug. 10, 2004

(54) ELECTROCHEMICAL CELL BUBBLE DETECTION

(75) Inventors: Stephen H. Broy, Riverside, CA (US); Michael A. Gonzalez, Pomona, CA (US); Mann Nguyen, Walnut, CA (US)

(73) Assignee: Teledyne Technologies Incorporated, Los Angeles, CA (US)

( * ) Notice: Subject to any disclaimer, the term of this patent is extended or adjusted under 35 U.S.C. 154(b) by 0 days.

(21) Appl. No.: 09/955,791

(22) Filed: Sep. 19, 2001

(51) Int. Cl.[7] .............................................. G01N 27/403
(52) U.S. Cl. ...................... 205/775; 204/401; 204/431
(58) Field of Search .......................... 205/775; 204/415, 204/431, 432, 412, 401

(56) References Cited

U.S. PATENT DOCUMENTS

| | | | | |
|---|---|---|---|---|
| 2,752,308 A | * | 6/1956 | Andrus | |
| 3,132,082 A | * | 5/1964 | Overmyer | |
| 3,410,778 A | * | 11/1968 | Krasberg | |
| 5,126,035 A | * | 6/1992 | Kiesele et al. | |
| 5,215,644 A | * | 6/1993 | Ashikaga | |
| 5,237,855 A | | 8/1993 | Gates | |
| 5,263,361 A | | 11/1993 | Gates | |
| 5,326,447 A | * | 7/1994 | Fletcher | |
| 5,583,635 A | | 12/1996 | Miura et al. | |
| 5,668,302 A | | 9/1997 | Finbow et al. | |
| 5,690,808 A | | 11/1997 | Akmal et al. | |

| | | | |
|---|---|---|---|
| 6,454,921 B1 | * | 9/2002 | Hodges et al. |

FOREIGN PATENT DOCUMENTS

| | | |
|---|---|---|
| JP | 58109875 | 6/1983 |
| JP | 59054936 | 3/1984 |
| JP | 3273135 | 12/1991 |
| JP | 4167087 | 6/1992 |

OTHER PUBLICATIONS

Esp@cenet Abstract for JP 58109875.
Esp@cenet Abstract for JP 59054936.
Esp@cenet Abstract for JP 3273135.
Esp@cenet Abstract for JP 4167087.

* cited by examiner

Primary Examiner—Alex Noguerola
(74) Attorney, Agent, or Firm—Kirkpatrick & Lockhart LLP (57) ABSTRACT

A method is provided for detecting imminent failure of an electrochemical cell, such as an electrochemical oxygen sensor, including detecting the presence of a gas pocket in/over the electrolyte within the cell either optically, by differences in the path of a light beam through the cell, due to the different refractive indices of air or nitrogen gas and electrolyte solutions or electrically, by loss of electrolyte between a pair of electrodes. An electrochemical cell assembly also is provided having a gas pocket detection assembly. Lastly, a method for retrofitting an electrochemical cell with a gas pocket detection assembly also is provided, along with a kit for retrofitting a cell with a gas pocket detection assembly.

33 Claims, 6 Drawing Sheets

ELECTROCHEMICAL CELL BUBBLE DETECTION

BACKGROUND OF THE INVENTION

1. Field of the Invention

The present invention relates to methods for detecting bubbles in electrochemical cells, a related apparatus and a method for retrofitting existing electrochemical cells with a bubble detection apparatus.

2. Description of the Related Art

A typical micro fuel cell oxygen sensor, also known as a galvanic electrochemical oxygen sensor, includes a cathode and an anode sealed in a housing (sensor body) filled with an appropriate electrolyte. Oxygen diffuses into the sensor body through a thin sensing membrane or electrode. Sensors of this type typically are sealed and are disposable. The sensors typically include: a lead anode, a noble metal cathode (gold or silver), an aqueous electrolyte solution, such as potassium hydroxide (KOH), a plastic body (container) with electrical contacts between the cathode and the anode and a diffusion barrier of Teflon or other materials as are known in the art.

Electrochemical oxygen sensors, as well any as other gas sensors and galvanic cells in which a liquid electrolyte is used, are susceptible to failure due to water loss which results in the formation of a gas pocket between the primary anode and cathode. In the case of oxygen sensors, as is the case with many galvanic cells, failure of the cell due to the formation of a gas pocket between the electrodes is expected, but the exact time of failure typically cannot be anticipated. In industrial systems, to replace a sensor a manufacturing process often must be shut down. The failure of an oxygen sensor, or other galvanic cell-type sensors or devices, causes costly and unpredictable operational shutdowns. Thus, a system is desired that automatically detects the formation of gas pockets in galvanic cells and sensors, such as electrochemical oxygen sensors, and therefore advises of imminent cell or sensor failure.

SUMMARY OF THE INVENTION

Provided herein is a method for detecting the presence of a gas pocket in an electrochemical cell, such as an oxygen sensor. The method may be used to predict imminent failure of the cell. In one embodiment, a light beam is directed through electrolyte in the cell between electrodes at an angle so that the light beam is refracted when no bubble is present in the electrolyte and is refracted to a lesser degree, or is not refracted, when a gas pocket is present in the path of the light beam.

In a second embodiment, a sensor electrode is placed in an area of the galvanic cell in which a gas pocket collects prior to failure of the cell. Imminent cell failure is detected by loss of electrical contact, due to loss of intervening electrolyte between the sensor electrode and a counter-electrode. The counter-electrode may be a primary electrode of the electrochemical cell.

Thus, the present invention is generally directed to an electrochemical cell assembly. The assembly includes an electrochemical cell that includes a container (sensor housing) having a wall defining an interior volume and typically, end portions, the cell includes a primary anode, a primary cathode and an electrolyte. The electrochemical cell assembly also includes a gas pocket detection assembly suitably configured to detect formation and/or enlargement of a gas pocket in the container. The detection assembly detects the gas pocket prior to failure of the electrochemical cell from loss of electrolyte contact (continuity) between the primary anode and the primary cathode resulting from further enlargement of the gas pocket.

In an electrical bubble detection embodiment within the present invention, the gas pocket detector assembly includes a secondary electrode suitably configured within the container to detect loss of electrolyte contact (continuity) between the secondary electrode and a detector counter-electrode prior to failure of the electrochemical cell due to loss of electrolyte contact between the primary anode and the primary cathode resulting from further enlargement of the gas pocket. In the embodiment, the detector counter-electrode may be a primary electrode.

In an optical bubble detection embodiment within the present invention, the wall of the container comprises a first clear portion and a second clear portion suitably configured so that a light beam can pass through the container. The gas pocket detector assembly includes a light beam source adjacent to the first clear portion. The light beam source is configured to direct a light beam on a path through the first clear portion and the second clear portion of the container. A light beam detector is configured to detect the light beam exiting from the container through the second clear portion. The detector is selected and/or configured to produce a first signal when the light beam travels a direct path through the interior of the container (when no gas pocket in the electrolyte is located in the path of the light beam) and second signal when the light beam travels a refracted path through the interior of the container (when a gas pocket is present in the electrolyte in the path of the light beam). The first signal and the second signal may be one of a signal generated when a light beam strikes a detector, or the lack of a signal when no light beam strikes the detector.

The present invention also provides a method for predicting failure of an electrochemical cell as described above. The method generally includes the step of providing a gas pocket detector assembly to detect formation of or enlargement of a gas pocket in the container prior to failure of the electrochemical cell due to loss of electrolyte contact between the anode and the cathode resulting from formation or enlargement of the gas pocket. In a second step of the method, the gas pocket detector assembly is used to monitor the cell for the formation or enlargement of a gas pocket in the container. The gas pocket detector assembly may be an electrical or optical detector, as described above.

In another embodiment, a method is provided for retrofitting an electrochemical gas sensor device including an electrochemical cell, as described above. The method includes the step of attaching a gas pocket detection assembly to the gas sensor device. The gas pocket detection assembly is suitably configured to detect formation or enlargement of a gas pocket in the container prior to failure of the electrochemical cell due to loss of electrolyte contact between the anode and the cathode resulting from further enlargement of the gas pocket.

Also provided is a kit for retrofitting an electrochemical gas sensor device. The kit may include a gas pocket detector assembly that is suitably configured to attach to a gas sensor device to detect formation or enlargement of a gas pocket in an electrochemical cell in the gas sensor device. The kit may include a bracket or brackets configured to engage a structure in the gas sensor device other than the electrochemical cell. The bracket or brackets position a light beam source so that the light beam source directs a light beam on a path through the interior volume of the container and/or position a light beam detector to detect the light beam exiting from the container. The detector may be selected and/or configured to produce a first signal when the light beam travels a direct path through the interior volume of the container and/or a second signal when the light beam travels a refracted path through the interior volume of the container.

BRIEF DESCRIPTION OF THE DRAWINGS

FIGS. 5A, 5B and 5C are cross-sectional elevational views, in schematic form, of a gas sensor having a secondary cathode as a gas pocket detector.

DETAILED DESCRIPTION OF THE PREFERRED EMBODIMENTS

Provided herein is a method for detecting gas bubbles and/or gas pockets (hereinafter collectively referred to as "gas pockets," and like phrases) in an electrochemical cell. In the case of an electrochemical gas sensor such as an oxygen sensor, water from the liquid electrolyte will slowly be removed (moving through the thin membrane or electrode and carried out by the flow of the sample gas). As the water is removed, a gas pocket will form. When the gas pocket develops, the anode-to-cathode path is interrupted and the sensor signal becomes noisy. The sensor current output then drops, making the sensor useless for proper oxygen measurement. Therefore, according to the present invention, prior to failure of the sensor, as the electrolyte levels drop to where failure is imminent, the gas pocket is detected, indicating the end or imminent end of the life of the sensor.

An electrochemical cell as described herein may be any type of electrochemical cell susceptible to failure due to the formation or enlargement of a gas pocket. A typical cell of this sort is an electrochemical gas sensor, such as an oxygen sensor of the type described in U.S. Pat. Nos. 5,668,302 and 5,690,808, both of which are incorporated herein by reference in their entirety. In any case, a typical electrochemical cell contains a primary anode, a primary cathode and an electrolyte liquid between the anode and cathode. Failure of the cell is caused by the formation of an air pocket between the electrodes, interfering with electrical current flow between the electrodes. The electrodes used to detect oxygen are referred to herein as primary electrodes as opposed to secondary or detector electrodes, which are used in one embodiment of the present invention for the detection of imminent failure of the electrode.

In one embodiment for detecting imminent failure of the electrode, refraction of light beam principle is used to determine the presence of a gas pocket of a threshold size in the electrochemical cell. The method exploits Snell's law, that is, differences in refractive indices between an electrolyte in an electrochemical cell and a gas that collects in such a cell, the collection of sufficient quantities of which can cause failure of that cell due to lack of intervening electrolyte between primary electrodes of the cell. In the method, a light beam is directed through a galvanic cell at an incident angle that typically is not normal to a point in the wall of the cell adjacent to the source of the light beam through which the light beam exits into the interior of the cell. When electrolyte is not present in the portion of the cell through which the light beam passes, the light beam is not refracted or is minimally refracted. This path is referred to herein as a direct path, since in that case, the light beam is not refracted or is minimally refracted on passage into the interior of the cell. When electrolyte is present in the portion of the cell through which the light beam passes, the light beam is refracted. This path is referred to herein as a refracted path, since in that instance, the light beam is refracted on passage into the interior of the cell. A light beam detector is provided, and is suitably positioned to determine whether or not the light beam is refracted.

In a second embodiment, a secondary cathode or anode is provided in the cell. This secondary electrode is positioned within the electrochemical cell so that when sufficient amounts of electrolyte are present, the secondary electrode is submerged in the electrolyte, completing a circuit with a counter-electrode, which may be a primary electrode of the cell. The secondary electrode is also positioned within the cell so that when a gas pocket develops or expands to the point that electrode failure is imminent, electrical contact between the secondary electrode and its counter-electrode is lost due to loss of electrolyte contact between the secondary electrode and its counter-electrode. At this point of imminent failure, the cell remains functional because electrical contact between the primary anode and primary cathode remains intact. Other gas bubble detection assemblies, based on optical, electrical or other technologies, may be used to detect the presence of gas pockets and bubbles in the electrochemical cell.

Figure 2:
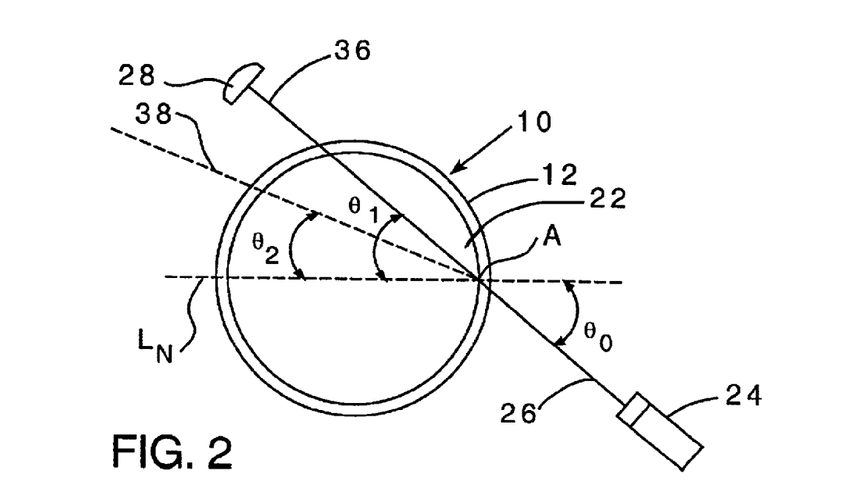
FIG. 2 is a cross-sectional plan view of the schematic form electrochemical gas sensor shown in FIG. 1.

In the first embodiment described herein, in which the gas pocket is identified optically by differential refraction, the electrochemical cell may be manufactured from a clear composition, such as acrylic, through which light may pass. As used herein in reference to walls of an electrochemical cell, "clear" and like words or phrases such as "clear portion", refers to the ability of the wall to allow passage of a light beam in detectable levels, and typically refers to, without limitation, transparence or translucence. Thus, walls of an electrochemical cell are "clear" if a light beam can pass through the cell, with or without electrolyte and/or an air pocket in the path of the light beam, at detectable levels, thereby permitting detection of whether the light beam is refracted at angles $\theta_1$ or at $\theta_2$ as shown in FIG. 2.

As used herein, all angles $\theta$ are in reference to a line normal to the surface of a point in the wall of the cell where the light beam exits the wall and enters the interior of the cell. Angle $\theta_0$ refers to the angle at which the light beam strikes the cell. Angle $\theta_1$ refers to the (direct) path of the light beam through the cell when a gas pocket is present in the path of the light beam. Angle $\theta_2$ refers to the (refracted) path of the light beam through the cell when no gas pocket is present in the path of the light beam.

It should be noted that the interior and exterior surfaces of the walls of the cell typically are parallel, and, therefore, the angle at which the light beam enters the wall of the cell at a given point is the same as the angle of the light beam exiting that point in the wall of the cell.

Nevertheless, it is preferred that the angle at which the light beam exits the wall of the cell into the interior of the cell is not normal to the interior surface of the wall of the cell at the point that the light beam passes into the interior so that the light beam can be differentially refracted whenever a gas pocket or bubble is present in the path of the light beam. If the light beam is normal to the interior surface of the wall, there is only one time differential refraction will be detected, when a bubble is present in the path of the light beam and the light beam scatters by passage through non-parallel walls of the bubble. By configuring the light beam source to direct a light beam that is not normal to the point of the interior surface of the wall of the container through which the light beam enters the cell, differential refraction will be detected 1) when a bubble is present in the path of the light beam and the light beam scatters minimally by passage through non-parallel walls of the bubble and 2) when a gas pocket is present which spans the entire portion of the interior of the cell through which the light beam passes.

By "substantially clear" and like words or phrases, it is meant that the portions of the walls of the cell through which the light is said to pass are "clear" in the sense described above. However, other portions of the walls of the cell might be opaque or may not transmit a light beam as would "clear" portions. These other portions may not be "clear" for a number of reasons, for instance and without limitation, they may have indicia thereupon, they may include electrodes or electrode leads or they may include other non-clear structures included in the electrochemical cell for any reason.

A typical electrochemical cell has a wall and two ends. In the first embodiment, the wall contains a first clear portion through which a light beam can pass into the cell. The wall also contains a second clear portion through which the light beam can pass when exiting the cell. Typically, the wall of the cell is prepared from a clear material, such as acrylic, so that the first clear portion and the second clear portion are portions of a clear wall with no actual boundary between the first and second clear portions, that is, they are contiguous.

The light source may be any light source capable of producing a beam, rather than divergent light (as is produced from a point light source). The light beam may be produced by a number of methods, but typically is a substantially parallel beam of a detectable wavelength or spectrum, such as a laser bean. Although a laser is preferred as a light beam source, any light source capable of producing a light beam will suffice so long as refraction of the beam is detectable according to the methods and apparatus described herein. For instance, a non-laser (divergent) light source may be combined, for example and without limitation, with a concave lens or a slotted mask to produce a suitable light beam. The light source may be an incandescent or fluorescent source, but preferably is a laser. An example of a suitable laser is a 650 nM, 5 mW laser module, commercially available, for instance, from Intelite, Inc. of Minden, Nev. Light sources typically are low wattage light sources due to the need for only limited light intensities.

Suitable detectors include any device capable of detecting a light beam and producing a signal, typically photoelectric cells. The detector typically is placed in relation to the cell and the light beam source so that the light beam passes through the walls of the cell and electrolyte within the cell and falls on the detector either when the light beam is refracted at angle $\theta_1$ or at angle $\theta_2$. The detector may be configured to fall within the path of the light beam at both angles $\theta_1$ or at $\theta_2$, so long as the detector, or the equipment to which the detector is attached, can distinguish between a light beam traveling at angle $\theta_1$ and at angle $\theta_2$. Alternately, two detectors may be configured to fall within the path of the light beam, one at angle $\theta_1$ and one at angle $\theta_2$. Detectors are widely available and typically have a built-in amplifier, such as those commercially available from Intelite, Inc.

In the second embodiment, in which the imminent failure of the electrochemical cell is detected by failure of an electrical detection circuit including a secondary electrode and a counter electrode. The secondary electrode may be any suitable electrode positioned to complete an electrical circuit with the counter-electrode, the circuit failure occurs when levels of electrolyte drop below a desired threshold. In gas sensors, the secondary electrode may be the same material as the primary electrode. For instance, in a typical oxygen sensor having a primary silver cathode and a primary lead anode, a second silver electrode may be used as a secondary electrode. So long as there is electrolyte between the primary anode and the secondary cathode, a detectable electric potential will be generated.

In another embodiment, an alarm circuit is provided that is operatively associated with the detector or detectors that monitor the light beam. The alarm circuit includes an analog-to-digital converter for converting an analog signal received from the detector or detectors into a digital signal. A comparator matches the converted digital signal, which is representative of refraction associated with the light beam, against a predefined reference signal. Based on the comparison of the converted digital signal to the predefined reference signal, an alarm condition may be detected that corresponds to the presence of a gas pocket or gas pockets. If an alarm condition is detected, then an indicator provides an audible, visual or audiovisual indication of the presence of the alarm condition.

Also provided herein is a method for retrofitting existing gas sensor devices with a gas pocket detection system as described herein. Typical gas sensor devices include a housing within which an electrochemical sensor is contained along with appropriate electronics. The retrofit method requires that the wall of the electrochemical cell includes clear portions, as described above, permitting passage of a light beam through the cell at a suitable path between the anode and cathode. The method includes configuring a light beam source to direct a light beam on a path through the cell, passing sequentially through the first clear portion, the interior of the cell and the second clear portion. The retrofit method also includes configuring a light beam detector so that the light beam exiting the second clear portion falls on the detector when a gas pocket is present in the path of the light beam and/or when no gas pocket is present in the path of the light beam. The detector is either capable of or configured to distinguish between a light beam passing through a gas pocket, where the beam is not refracted or is minimally refracted, and a light beam that does not pass through a gas pocket, where the beam is refracted, by generating a different signal depending upon the path of the light beam through the container due to the presence or absence of an air pocket in the path of the light beam.

A system or kit for retrofitting a sensor may be used to upgrade an existing gas detector device containing an electrochemical cell as described above. The kit contains a bracket adapted to engage a structure in a housing in which the gas sensor is contained, to align a light source and detector in the manner described above, to detect the presence of a gas pocket between electrodes in the electrochemical cell. The kit may include a bracket or brackets, tailored for a specific sensor device and electrochemical cell and optionally contains a light source, a detector and/or an electrochemical cell as described above.

Figure 1:
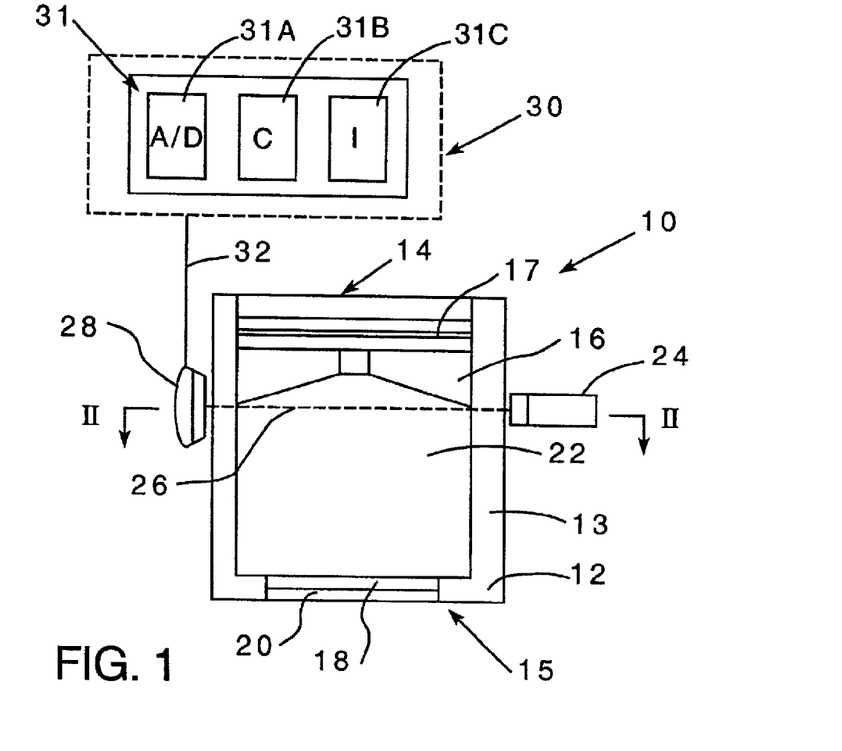
FIG. 1 is a cross-sectional elevational view, in schematic form, of a typical electrochemical gas sensor according to one embodiment of the present invention.

FIG. 1 is a schematic diagram of a typical electrochemical sensor 10 system according to the present invention. In FIGS. 1–5, like reference numbers refer to like elements. Sensor 10 includes a container 12 that includes a wall 13, a first end 14 and a second end 15. A lead anode 16 and rear expansion membrane 17 are provided adjacent the first end 14 and a cathode 18 and a gas permeable membrane 20 are provided adjacent to the second end 15. In the interior 22 of the container 12, between anode 16 and cathode 18 is provided an electrolyte. A laser 24 is provided to direct a laser beam 26 through container 12 and onto a detector 28, typically an amplified detector. The detector is electrically connected to a computer 30 by a lead 32. Detector 28 is suitably configured to fall within the path of laser beam 26 and, therefore, to send a different signal to computer 30 depending upon whether laser beam 26 is refracted or not. In use, when laser beam 26 falls onto detector 28, an electrical signal is generated and is passed to computer 30 via lead 32. Computer 30 contains hardware and software for generating an alarm indicating that gas pockets are present in electrolyte.

In one embodiment, an alarm circuit 31 is provided in the computer 30 for indicating an alarm condition associated with refraction of the laser beam 26, that is, the presence of a gas pocket or pockets. The alarm circuit 31 can include an analog-to-digital converter 31A, which is employed to convert an analog electrical signal received from the detector 28 through the lead 32. The converted digital signal, which is representative of the degree of refraction of the laser beam 26, is then transmitted to a comparator 31B. The comparator 31B compares the converted digital signal against a predefined reference signal to determine whether an alarm condition exists in connection with refraction of the laser beam 26. It can be appreciated that the characteristics of the predefined reference signal are selected as a function of the nominal condition of the laser beam 26, that is, for the nominal condition when a gas pocket or pockets are not present in the electrolyte. Hence, some measured difference between at least one characteristic of the converted digital signal and an equivalent characteristic of the predefined reference signal (e.g., a comparison of the respective amplitudes of the two signals), can be designated to trigger an alarm condition. Based on the output of the comparator 31B, an indicator 31C can be provided to generate an alarm if an alarm condition is detected. The alarm generated by the indicator 31C can be audible, visual or some reasonable combination of both audible and visual alarms. For example, a dialog box (not shown) accompanied by an audible chime can be generated on the computer 30 when an alarm condition is detected. It can be understood that the components of the alarm circuit 31 can be embodied in hardware, software or a combination of hardware and software installed on the computer 30. In this manner, the electrochemical cell can be monitored for the development of, or enlargement of a gas pocket.

FIG. 2 is a view of the sensor system of claim 1, showing the path of laser beam 26 through container 12. Shown is laser beam path 36 indicating the path of laser beam 26 when a gas pocket is present in the interior 22. Laser beam path 38 indicates the path of laser beam 26 when no gas pocket is present in the interior 22. According to Snell's law, when an air pocket is present in the path of laser beam 26 and directed to a surface of container 12 at angle $\theta_0$, (all angles $\theta$ are in relation to normal line $L_N$, normal to a tangent at point A, the point at which laser beam 26 enters the interior 22 of container 12) will pass along path 36, at angle $\theta_1$, which is approximately equal to $\theta_0$. When electrolyte is present in the interior 22 of container 12, in the path of laser beam 26, the laser beam will follow refracted path 38, where $\theta_2$ is less than $\theta_1$. As a result, laser beam 26 will not strike the detector 28 unless a gas pocket is present in the path of laser beam 26. A gas pocket or bubbles that do not span the complete interior 22 of the container 12 will refract or scatter laser beam 26 to varying extents depending upon the position of the bubble in the interior 22. In that case, detector 28 will send a noisy signal to computer 30 indicating the presence of the bubble in the interior 22.

Figure 3A:
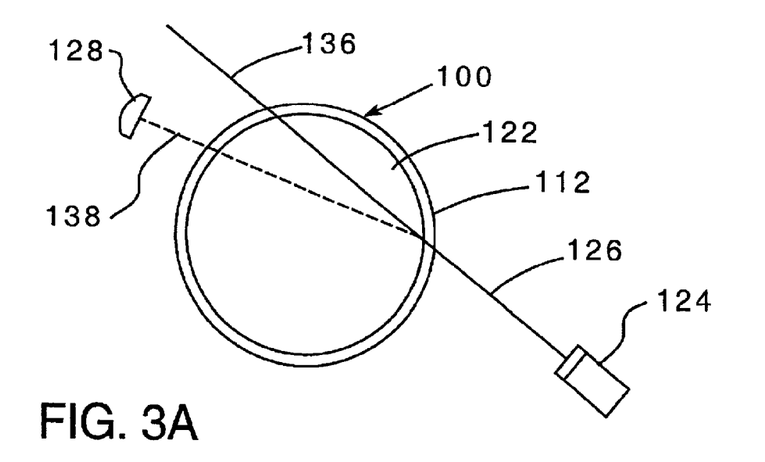
FIGS. 3A, 3B and 3C are cross-sectional plan views of gas sensors constructed according to the present invention, shown in schematic form having different detector configurations.
Figure 3B:
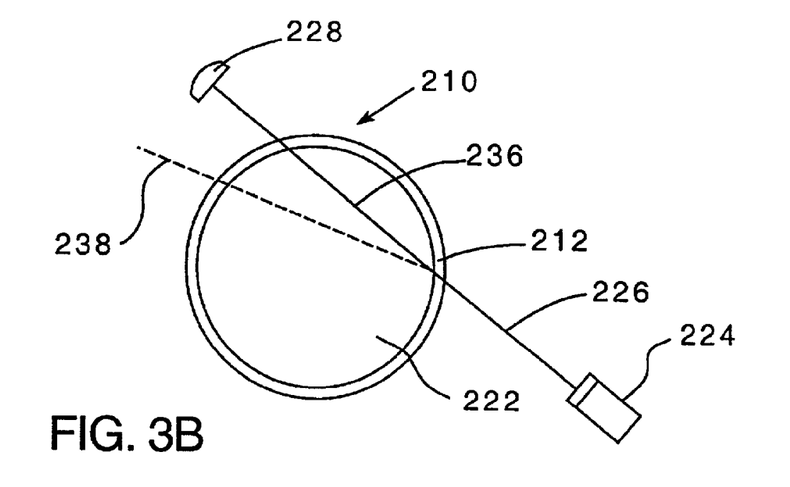
Figure 3C:
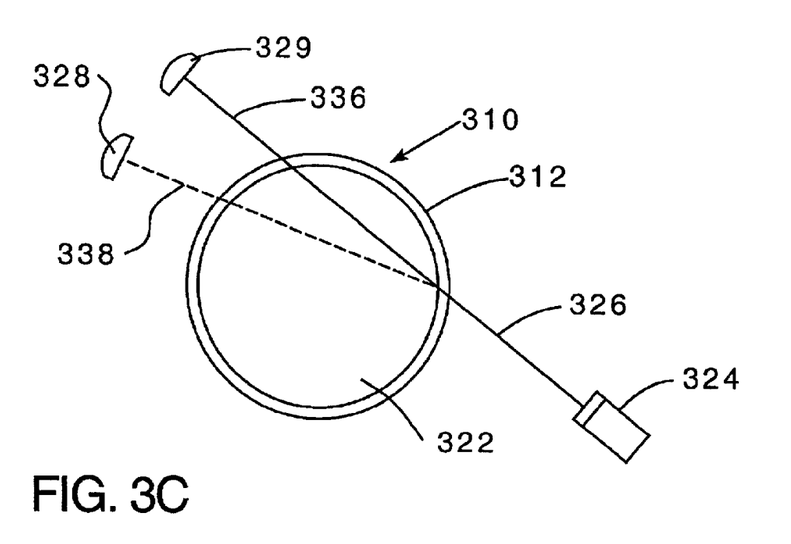

FIGS. 3A through 3C show variations of the embodiment shown in FIGS. 1 and 2. FIG. 3A shows a sensor 110 in which a laser 124 directs a laser beam 126 through interior 122 of container 112, along path 136 or refracted path 138 to strike detector 128 when no gas pocket is present in interior 122. FIG. 3B shows a sensor 210 in which a laser 224 directs a laser beam 226 through interior 222 of container 212, along path 236 or refracted path 238 to strike detector 228 when a gas pocket is present in interior 222. FIG. 3C shows a sensor 310 in which a laser 324 directs a laser beam 326 through interior 322 of container 312, along path 336 or refracted path 338 to strike detector 328 when a gas pocket is present in interior 322 and detector 329 when no gas pocket is present in interior 322.

Figure 4A:
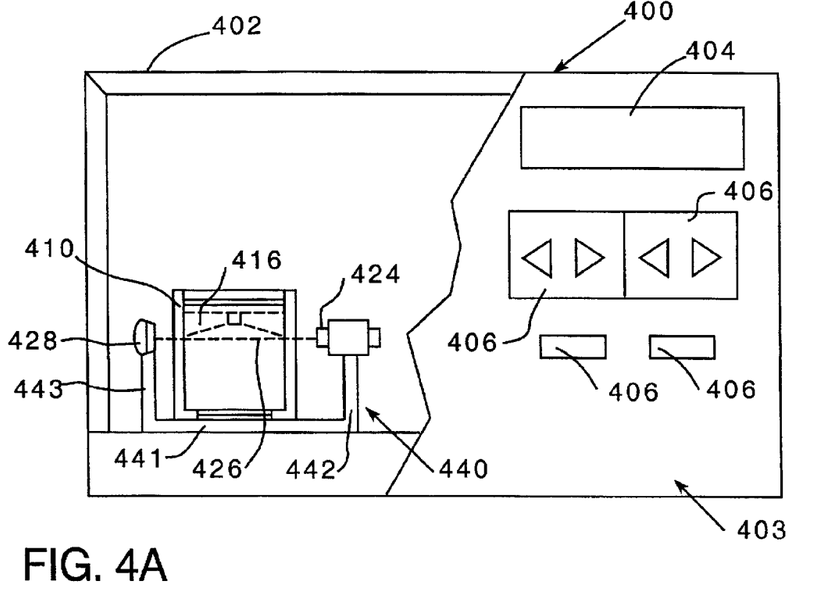
FIG. 4A is a partial-breakaway elevational view of a gas bubble detection device constructed according to the present invention.

FIG. 4A shows a gas sensor device 400, in schematic form, including a gas pocket detector including a housing 402, a sensor 410 and a gas pocket detection assembly 440. For clarity, sensor device 400 is shown schematically. Many elements of gas assembly 400 are omitted for clarity, such as electrical leads and components and assemblies for gas passage, such as tubes leading into and from sensor 410. Sensor 410 is substantially configured as sensor 10 of FIG. 1. Gas sensor device 400 includes a housing 402 and a faceplate 403 having a display 404, such as an LED display for indicating the status of the device 400 and/or detected gas levels. Touchpads 406 are provided for user input into the gas sensor device 400. Sensor 410 includes an anode 416, shown in phantom. Gas pocket detection assembly 440 includes bracket 441. Bracket 441 includes laser arm 442 and detector arm 443 respectively adapted to hold laser 424 and detector 428 in an appropriate orientation as described herein to differentially detect the presence of or absence of a gas pocket in sensor 410 by differential refraction of laser beam 446, shown in phantom.

Figures 4B, 4C:
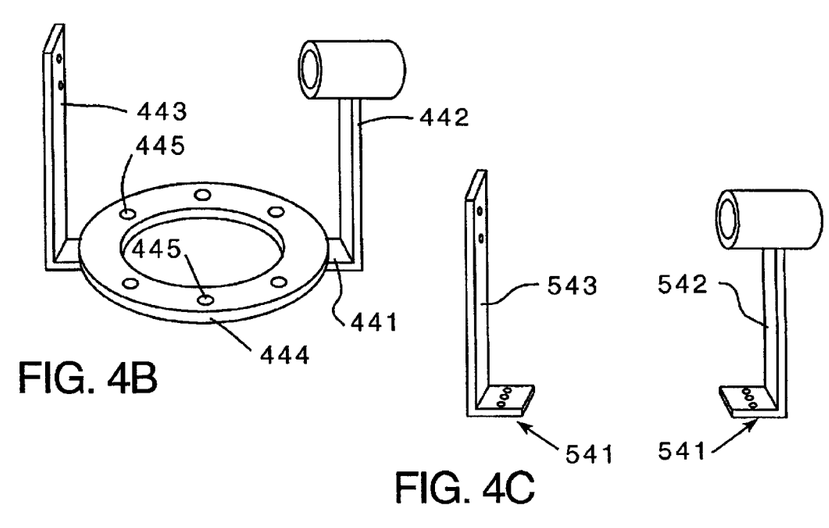
FIGS. 4B and 4C are elevational views, in schematic form, of two embodiments of retrofit brackets for a gas bubble detection device constructed according to the present invention

FIG. 4B shows bracket 441 of FIG. 4A. In FIG. 4A, sensor 410 is shown atop bracket 441, which is suitably configured to avoid blocking gas access to a gas permeable membrane of the sensor (not shown). Bracket 441 includes laser arm 442 and detector arm 443. Base portion 444 of bracket 441 is annular shaped so as not to cover a centrally disposed gas permeable membrane of a sensor that sits upon bracket 441. Holes 445 are provided to facilitate attachment of bracket 441 to the gas sensor device housing with fasteners (not shown). Bracket 441 is shown in one configuration that depicts its function. In practice, bracket 441 may be configured in any suitable fashion to fit any particular gas sensor device. Bracket 441 may be a single piece or two pieces, as shown in FIG. 4C in which the laser arm 542 and the detector arm 543 are separate brackets 541. In any case, configuration of the bracket(s) would depend upon the configuration of the gas detection device, and would naturally vary as a matter of design choice.

Figure 5A:
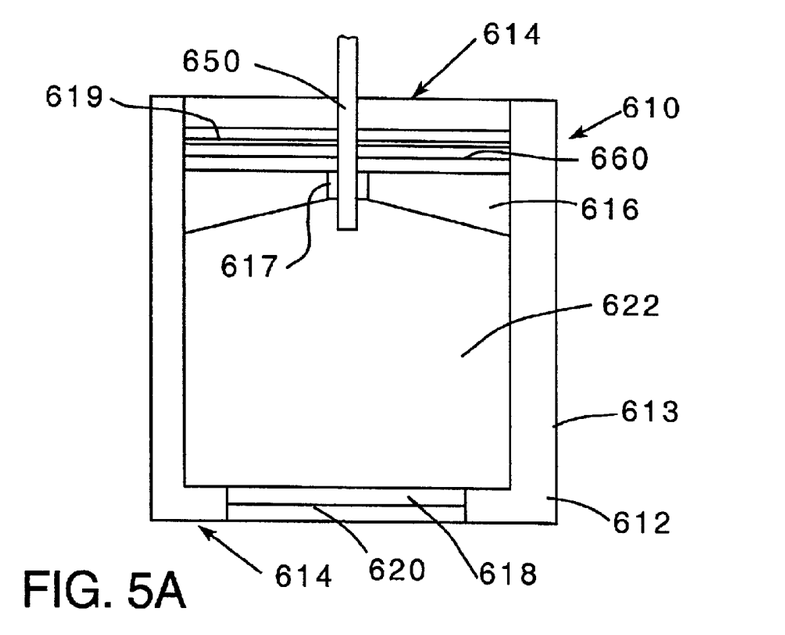
FIG. 5A shows an operable gas sensor.
Figure 5B:
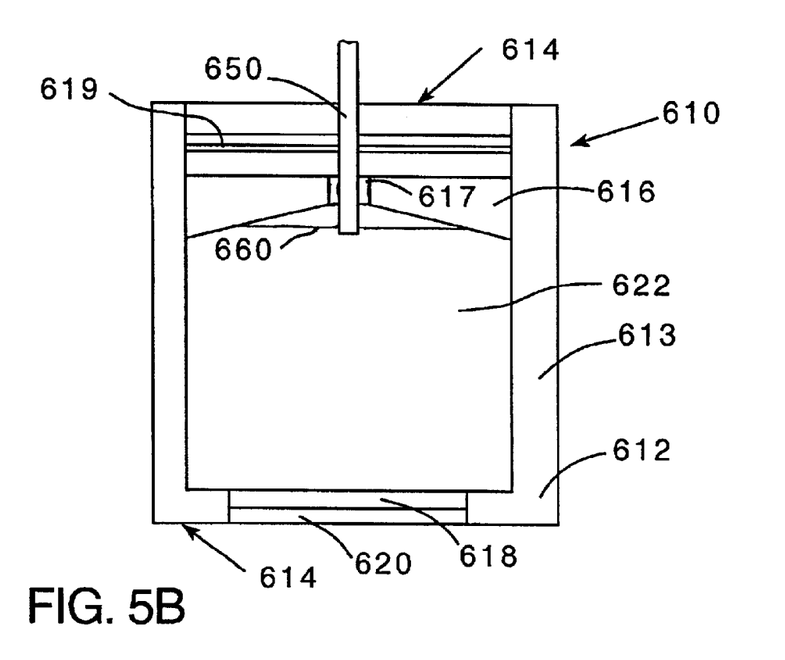
FIG. 5B shows an operable gas sensor with failure imminent.
Figure 5C:
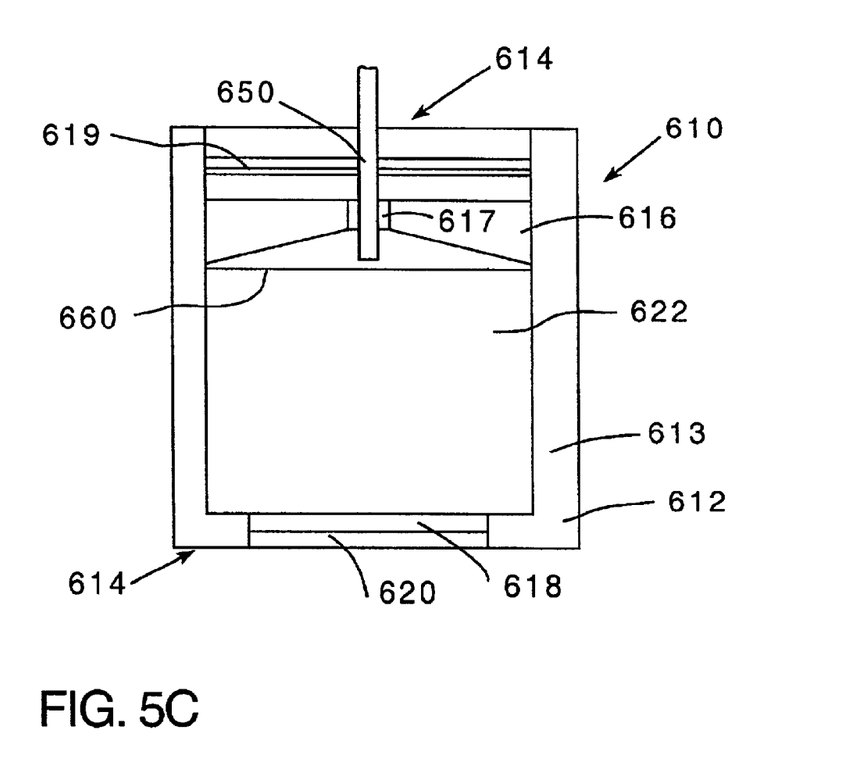
FIG. 5C shows a failed gas sensor.

FIGS. 5A–5C depict schematically a second embodiment of the present invention in which a secondary electrode is used to detect imminent failure of the cell. As above, the sensor 610 includes a container 612 that includes a wall 613, ends 614, a primary lead anode 616 having a passageway 617, a silver primary cathode 618, rear expansion membrane 619, a gas permeable Teflon membrane 620 and an interior 622 containing electrolyte 623. Sensor 610 also includes a secondary silver cathode 650 inserted into passageway 617, but not in contact with primary anode 616. The surface 660 of electrolyte 623 is indicated in each of FIGS. 5A, 5B and 5C. In FIG. 5A, the electrolyte surface 660 is above primary anode 616, indicating that the sensor is operable. As such, an electrical potential exists between primary anode 616 and second cathode 650. FIG. 5B shows an operable sensor 610 in which failure is imminent. Electrolyte surface 660 is below second cathode 650, so that no electrical potential exists between primary anode 616 and second cathode 650. Sensor 610 shown in FIG. 5B has not failed since electrolyte 623 is present between primary anode 616 and primary cathode 618. FIG. 5C shows an inoperable sensor in which electrolyte surface 660 has fallen below primary anode 616.

The above invention has been described with reference to the preferred embodiment. Obvious modifications and alterations will occur to others upon reading and understanding the preceding detailed description and the claims. It is intended that the invention be construed as including all such modifications and alterations.

We claim:

1. An electrochemical cell assembly, comprising:
    a. an electrochemical cell comprising a container comprising a wall defining an interior volume, electrolyte contained within the interior volume, an anode and a cathode, the cell having a right path that passes through the wall and a portion of the interior volume of the container in which gas collects before or during failure of the electrochemical cell from loss of the electrolyte from the interior volume; and
    b. a gas pocket detection assembly comprising:
        (i) a light beam source aligned to direct a light beam along the light path; and
        (ii) a light beam detector configured to detect the light beam exiting the container and to produce a first signal when the light beam travels a direct path through the interior volume of the container when no gas pocket is present in the light path and a second signal when the light beam travels a refracted path through the interior volume of the container when a gas pocket is present in the electrolyte in the light path.

2. The electrochemical cell assembly of claim 1, wherein the light beam source is a laser.

3. The electrochemical cell of claim 1, wherein the wall is substantially clear.

4. The electrochemical cell of claim 1, wherein the container is cylindrical and has end portions, the well is annular, and the anode and cathode are located adjacent to the end portions.

5. The electrochemical cell of claim 4, wherein the annular wall is substantially clear.

6. The electrochemical cell of claim 1, wherein the light beam detector is located in the refracted path and not in the direct path.

7. The electrochemical cell of claim 1, wherein the light beam detector is located in the direct path and not in the refracted path.

8. The electrochemical cell of claim 1, wherein the light beam detector is located in the direct path and a second light beam detector is located in the refracted path.

9. The electrochemical cell of claim 1, further comprising an alarm circuit in electrical communication with the gas pocket detection assembly to monitor the cell for the presence of a gas pocket in the light path.

10. The electrochemical cell assembly of claim 1, wherein the electrochemical cell is a gas sensor.

11. The electrochemical cell assembly of claim 1, wherein the gas sensor is an oxygen sensor.

12. A method for predicting failure of an electrochemical cell comprising a container having a wall defining an interior volume, electrolyte contained within the interior volume, an anode and a cathode, comprising the steps of:
    a) passing a light beam through a light path in the interior volume, wherein the light path passes through a portion of the interior volume of the container in which gas collects before or during failure of the electrochemical cell from loss of electrolyte from the interior volume; and
    b) detecting differences in the path of the light beam with a light beam detector configured to detect the light beam exiting the container and to produce a first signal when the light beam travels a direct path through the interior volume of the container when no gas pocket is present in electrolyte in the light path and a second signal when the light beam travels a refracted path through the interior volume of the container when a gas pocket is present in electrolyte in the light path.

13. The method of claim 12, wherein the light beam source is a laser.

14. The method of claim 12, wherein the wall is substantially clear.

15. The method of claim 12, wherein the container is cylindrical and has end portions, the wall is annular, and the anode and the cathode are located adjacent to the end portions.

16. The method of claim 15, wherein the annular wall is substantially clear.

17. The method of claim 12, wherein the light beam detector is located in the refracted path and not in the direct path.

18. The method of claim 12, wherein the light beam detector is located in the direct path and not in the refracted path.

19. The method of claim 12, wherein the light beam detector is located in the direct path and a second light beam detector is located in the refracted path.

20. The method of claim 12, further comprising an alarm circuit in electrical communication with the gas pocket detection assembly to monitor the cell for one of formation and enlargement of a gas pocket in the container.

21. The method of claim 12, wherein the electrochemical cell is a gas sensor.

22. The method of claim 21, wherein the gas sensor is an oxygen sensor.

23. A method for detecting gas bubbles in an electrochemical cell that comprises a wall defining an internal volume, an anode, a cathode and an electrolyte contained within the internal volume, the method comprising the step of directing a light beam on a light path that passes through a portion of the interior volume where gas collects before or during failure of the electrochemical cell from loss of electrolyte from the interior volume and at one or more light beam detectors, wherein one or more light beam detectors are configured to produce a first signal when a gas pocket is located in the light path and a second signal when no gas pocket is located in the light path.

24. The method of claim 23, wherein the light beam is a laser beam.

25. The method of claim 23, wherein the electrochemical cell is a gas sensor.

26. The method of claim 23, wherein the electrochemical cell is an oxygen sensor.

27. A method for retrofitting an electrochemical gas sensor assembly comprising an electrochemical cell comprising a container having a wall defining an interior volume, an anode, a cathode and electrolyte contained within the interior volume, the container having a light path passing through the wall and a portion of the interior volume of the container in which gas collects before or during failure of the electrochemical cell from loss of electrolyte from the interior volume, the method comprising the step of attaching a gas pocket detection assembly to the gas sensor, the gas pocket detection assembly comprising:
  (i) a light beam source aligned to direct a light beam along the light path; and
  (ii) a light beam detector configured to detect the light beam exiting the container and to produce a first signal when the light beam travels a direct path through the interior volume of the container when no gas pocket is present in the light path and a second signal when the light beam travels a refracted path through the interior volume of the container when a gas pocket is present in the electrolyte in the light path.

28. An apparatus for retrofitting an electrochemical gas sensor device including an electrochemical cell comprising a container having a wall defining an interior volume, an anode, a cathode and an electrolyte contained within the interior volume, the container having a light path passing through the wall and a portion of the interior volume of the container in which gas collects before or during failure of the electrochemical cell from loss of electrolyte from the interior volume, the apparatus comprising parts of a gas pocket detector assembly, the parts comprising:
  (a) a light beam source;
  (b) a light beam detector; and
  (c) a bracket or brackets configured to:
    (i) engage the light beam source and to position the light beam source to direct a light beam along the light path through the interior volume; and
    (ii) engage a light beam detector and position the light beam detector to detect a light beam from the light beam source exiting the container from the interior volume so that the detector produces a first signal when the light beam travels a direct path through the interior volume of the container when no gas pocket in the electrolyte is located in the light path and a second signal when the light beam travels a refracted path through the interior volume when no gas pocket is present in the electrolyte in the light path.

29. The apparatus of claim 28, wherein the light beam source is a laser.

30. The apparatus of claim 28, wherein the electrochemical cell is a gas sensor.

31. The apparatus of claim 30, wherein the electrochemical cell is an oxygen sensor.

32. The apparatus of claim 30, further comprising an electrochemical cell.

33. The apparatus of claim 30, further comprising computer software and/or hardware comprising an alarm circuit in electrical communication with the gas pocket detection assembly to monitor the cell for the presence of a gas pocket in the light path.

* * * * *

UNITED STATES PATENT AND TRADEMARK OFFICE
CERTIFICATE OF CORRECTION

PATENT NO. : 6,773,577 B1 Page 1 of 1
DATED : August 10, 2004
INVENTOR(S) : Broy et al.

It is certified that error appears in the above-identified patent and that said Letters Patent is hereby corrected as shown below:

Column 1,
Line 25, "any as" should read -- as any --

Column 3,
Line 26, "invention" should read -- invention. --

Column 4,
Line 49, "portion", should read -- portion, --

Column 5,
Line 47, "bean." should read -- beam. --

Column 8,
Line 1, "$L_N$" should read -- $L_N$ --

Column 9,
Line 32, "right" should read -- light --
Line 54, "well" should read -- wall --

Column 10,
Line 7, "1" should read -- 10 --

Signed and Sealed this

Twenty-eighth Day of June, 2005

JON W. DUDAS
*Director of the United States Patent and Trademark Office*